United States Patent
Mayer et al.

(10) Patent No.: US 11,123,131 B2
(45) Date of Patent: Sep. 21, 2021

(54) INSTRUMENT FOR GRASPING, DISSECTING AND/OR COAGULATING BIOLOGICAL TISSUE

(71) Applicant: Erbe Elektromedizin GmbH, Tübingen (DE)

(72) Inventors: Volker Mayer, Tübingen (DE); Rolf Weiler, Kusterdingen (DE)

(73) Assignee: Erbe Elektromedizin GmbH, Tubingen (DE)

( * ) Notice: Subject to any disclaimer, the term of this patent is extended or adjusted under 35 U.S.C. 154(b) by 232 days.

(21) Appl. No.: 15/254,533

(22) Filed: Sep. 1, 2016

(65) Prior Publication Data
US 2017/0065331 A1    Mar. 9, 2017

(30) Foreign Application Priority Data

Sep. 3, 2015 (EP) .................................. 15183777

(51) Int. Cl.
*A61B 18/14* (2006.01)
*A61B 17/29* (2006.01)
*A61B 18/00* (2006.01)

(52) U.S. Cl.
CPC .......... *A61B 18/1445* (2013.01); *A61B 17/29* (2013.01); *A61B 18/1482* (2013.01);
(Continued)

(58) Field of Classification Search
CPC ... A61B 18/1445; A61B 18/085; A61B 17/29; A61B 2018/0225; A61B 18/1442;
(Continued)

(56) References Cited

U.S. PATENT DOCUMENTS 6,602,252 B2   8/2003   Mollenauer
8,858,553 B2   10/2014   Chojin
(Continued)

FOREIGN PATENT DOCUMENTS

CN    101969874 A    2/2011
CN    103429182 A    12/2013
(Continued)

OTHER PUBLICATIONS

European Search Report in corresponding European Application No. 15183777, dated Feb. 9, 2016, 9 pages.
(Continued)

*Primary Examiner* — Eun Hwa Kim
*Assistant Examiner* — Catherine Premraj
(74) *Attorney, Agent, or Firm* — Fitch, Even, Tabin & Flannery LLP

(57) ABSTRACT

A tool (16) for the coagulation and dissection of biological tissue including a counter-bearing (35) that has at least one recess (37) open toward the outside and/or one or more hollow chambers (63). The recess (37) or the hollow chamber (63) is configured to provide a force/path elasticity characteristic curve with a plateau-like region II, V, during compression and reexpansion. The path section x in which the elasticity characteristic curve indicates the plateau II, IV preferably is as long as the tissue to be dissected is thick, and is, for example, in the range of 0.2 to 1.5 mm. As a result, the force exerted on the tissue during the cutting operation remains substantially constant in the effective work region.

13 Claims, 5 Drawing Sheets

(52) U.S. Cl.
CPC . *A61B 2017/294* (2013.01); *A61B 2018/0063* (2013.01); *A61B 2018/00589* (2013.01); *A61B 2018/00601* (2013.01); *A61B 2018/00607* (2013.01); *A61B 2018/1457* (2013.01)

(58) Field of Classification Search
CPC ...... A61B 2018/00607; A61B 18/1482; A61B 2017/294; A61B 2018/00589; A61B 2018/00601; A61B 2018/0063; A61B 2018/1457
See application file for complete search history.

(56) References Cited

U.S. PATENT DOCUMENTS

| | | | |
|---|---|---|---|
| 10,130,414 | B2 | 11/2018 | Weiler et al. |
| 2003/0144660 | A1* | 7/2003 | Mollenauer ...... A61B 17/07207 606/45 |
| 2004/0049185 | A1 | 3/2004 | Latterell et al. |
| 2005/0113826 | A1* | 5/2005 | Johnson ............. A61B 18/1442 606/45 |
| 2005/0171533 | A1 | 8/2005 | Latterell et al. |
| 2009/0234355 | A1 | 9/2009 | Edwards et al. |
| 2009/0248007 | A1* | 10/2009 | Falkenstein ........ A61B 18/1442 606/33 |
| 2012/0059374 | A1 | 3/2012 | Johnson et al. |
| 2013/0014375 | A1* | 1/2013 | Hempstead ........ A61B 18/1442 29/458 |
| 2013/0046295 | A1 | 2/2013 | Kerr et al. |
| 2014/0194875 | A1* | 7/2014 | Reschke ............ A61B 18/1445 606/45 |
| 2014/0214025 | A1* | 7/2014 | Worrell .............. A61B 18/1445 606/41 |
| 2015/0374430 | A1 | 12/2015 | Weiler et al. |

FOREIGN PATENT DOCUMENTS

| | | |
|---|---|---|
| CN | 104382648 A | 3/2015 |
| EP | 2959854 A1 | 12/2015 |
| JP | 2004-180843 A | 7/2004 |
| JP | 2005-514102 A | 5/2005 |
| JP | 2011-156363 A | 8/2011 |
| JP | 2016-7542 A | 1/2016 |

OTHER PUBLICATIONS

Russian Office Action and Search Report dated Aug. 14, 2019, in corresponding Russian Application No. 2016135723/14(056050), with English translation (11 pages).

Chinese Office Action dated Dec. 25, 2019 and Search Report dated Dec. 16, 2019, in corresponding Chinese Application No. 201610789088.9, with machine English translation (16 pages).

Japanese Notice of Reasons for Refusal dated Jan. 31, 2020, in corresponding Japanese Application No. 2016-164189, with English translation (16 pages).

* cited by examiner

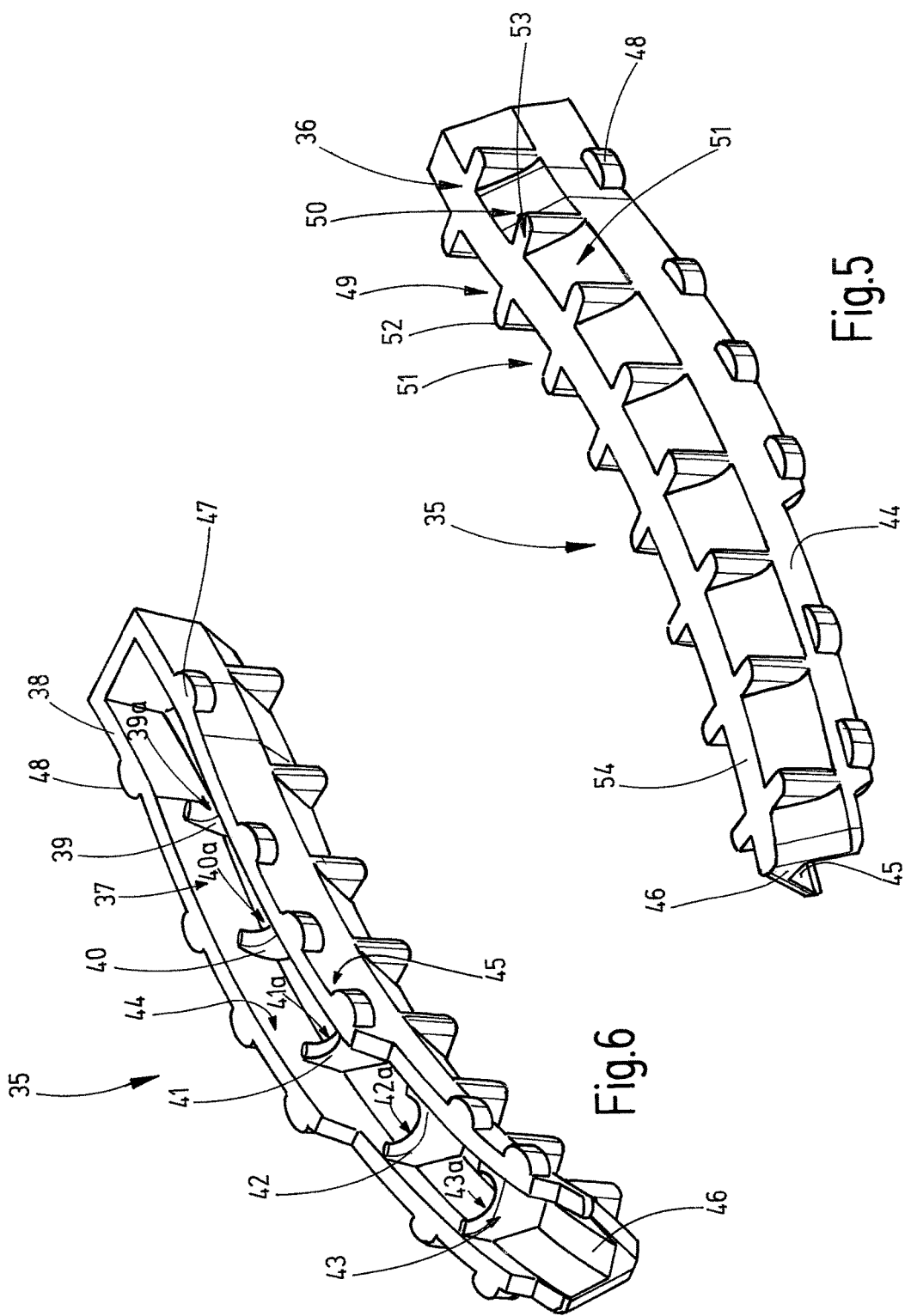

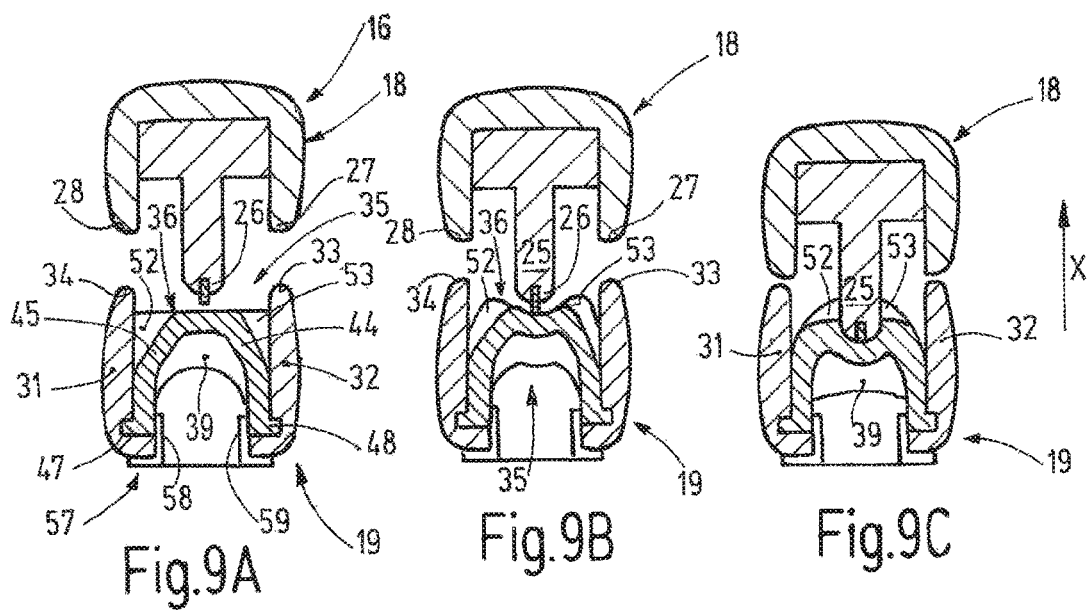
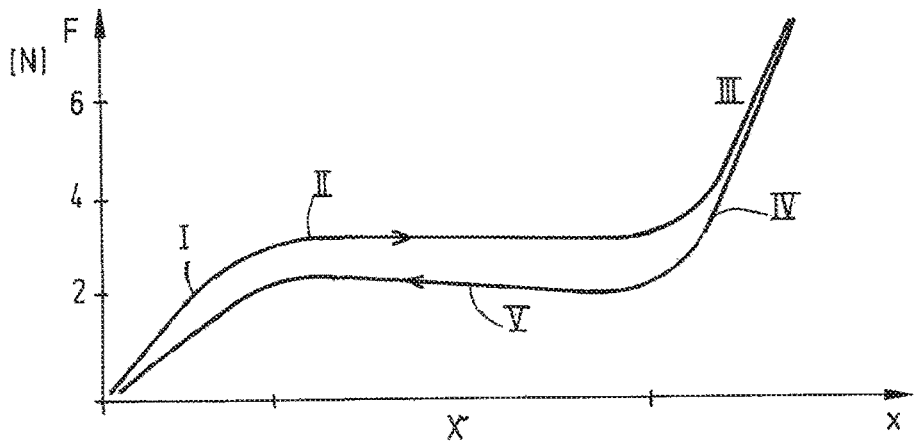
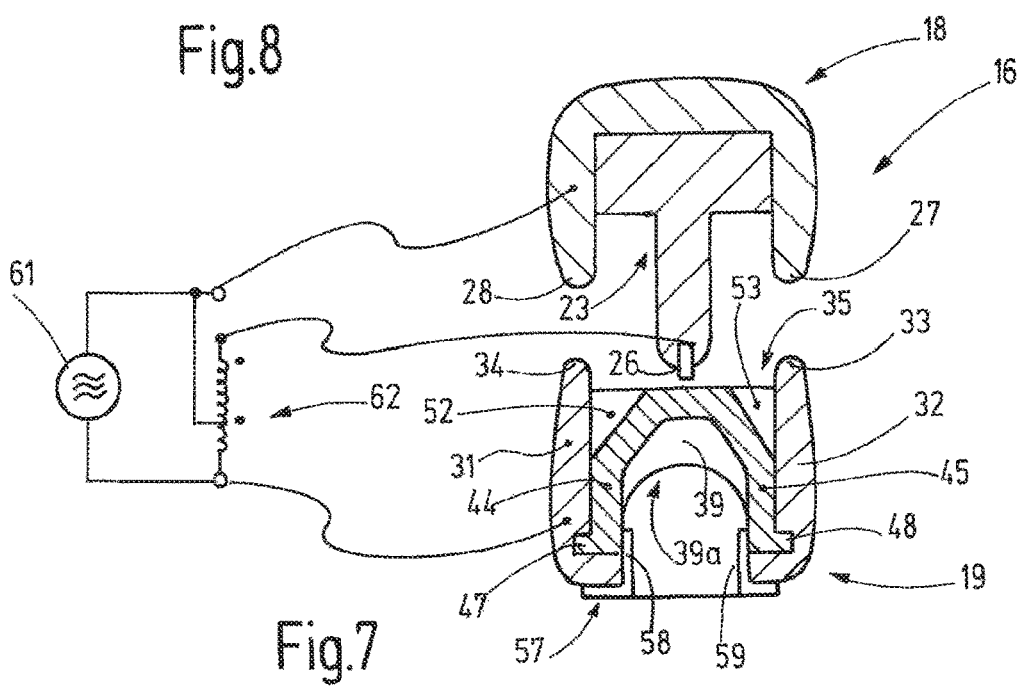

INSTRUMENT FOR GRASPING, DISSECTING AND/OR COAGULATING BIOLOGICAL TISSUE

RELATED APPLICATION(S)

This application claims the benefit of European Patent Application No. 15183777.0 filed Sep. 3, 2015, the contents of which are incorporated herein by reference as if fully rewritten herein.

TECHNICAL FIELD

The invention relates to a manually guided or machine-guided instrument with which biological tissue can be grasped, coagulated and dissected, or only coagulated.

BACKGROUND

Such an instrument that is configured as scissors has been known from document US 2004/0049185 A1. The instrument has two branches that are connected to each other via a hinge and can thus be pivoted toward each other and away from each other. The branches are able to grasp tissue between them. Each of the two branches has an approximately U-shaped cross-section, wherein the ends of the limbs of the U-shaped cross-section form the coagulation electrodes. These coagulate tissue grasped between them when the two branches are connected to the terminals of a corresponding electrical power source.

In addition, one of the branches comprises a cutting electrode that is arranged centrically between the coagulation electrodes so as to project beyond them. The opposing branch comprises a counter-bearing of an elastic material into which may penetrate the cutting electrode while elastically deforming the elastic material. In doing so, the biological material located in front of the cutting electrode is pressed against the cutting electrode.

Furthermore, document US 2005/0171533 A1 discloses a similar instrument with two branches, each of them bearing coagulation electrodes and, and one cutting electrode that is arranged in one of the branches between two coagulation electrodes. The oppositely located branch is provided with a groove for the accommodation of the cutting electrode. At the bottom of the groove, there is arranged an isolator of elastic material.

Considering the instruments having the aforementioned design the cutting operation of the grasped tissue takes place between the cutting electrode and the counter-bearing. In doing so, it is important that the tissue be dissected safely and completely due to the effect of the electric current coming from the cutting electrode, in which case a mechanical cutting action of the cutting electrode is not desired. In the practical application, the amount and/or thickness, as well as the quality, of the tissue grasped between the two branches is subject to certain variations. Still, despite these changing conditions, a clean cut of the tissue and a good coagulation of the tissue seams is to be achieved. In order to achieve good coagulation, the tissue must be grasped with relatively great force between the coagulation electrodes. In contrast, a clearly lower force is desired on the cutting electrode.

SUMMARY

Considering this, the object of the invention is to provide a concept for a machine-guided or manually guided instrument with which the mentioned requirements can be fulfilled.

The instrument comprises a first branch with at least one coagulation and/or sealing electrode for the coagulation of biological material. Preferably arranged on the first branch are two first sealing electrodes that extend at distance from each other and between which a free space is formed. A preferably electrically insulating cutting electrode carrier is arranged in the free space, said carrier bearing the cutting electrode. To do so, the cutting electrode carrier may have a central wall-like projection extending beyond the sealing electrodes, said projection bearing the cutting electrode on its free end.

The second branch has at least one second sealing electrode, preferably two sealing electrodes arranged at a distance from each other. In the free space existing between the second sealing electrodes, there is a arranged a counter-bearing that, preferably, is made as a separate, prefabricated element of elastic material. This counter-bearing has at least one recess that is open toward the outside and/or at least one hollow chamber. These one or more recesses and/or hollow chambers can be used for the targeted adjustment of the elasticity characteristic curve of the counter-bearing. In doing so, it can be achieved that the force exerted by the counter-bearing in the target operating range directed against the cutting element or the cutting electrode, does not go below a limit of 1 N to 2 N, for example, during the entire cutting operation and does not exceed a limit of 3 N or 4 N and 7 N or 8 N, respectively, for example. In the instrument, the cutting element and the counter-bearing are mechanically coupled by the mouth part. This means that, via the angled relative arrangement, the counter-bearing is always compressed by the cutting electrode into a kind of walk movement, i.e., not, and preferably never, compressed in a completely parallel manner. Therefore, when looking at the elasticity behavior of the counter-bearing and, in particular, its geometric configuration, it makes sense to look at only a very short, infinitesimally small segment of the counter-bearing. Using this look at a counter-bearing segment, a non-linear force/path characteristic when compressing the counter-bearing can be achieved. In particular, this force/path characteristic may comprise a section with almost constant force. A straight line applied to this section does not intersect the zero point of the force/path diagram. In the ideal case, such a straight line extends almost parallel to the path-axis (abscissa). Accordingly, the force/path characteristic has a plateau.

One or more recesses and/or one or more hollow chambers may be provided in the counter-bearing. The recesses are open toward the outside, i.e., they are not enclosed on all sides by the counter-bearing but occur as opening on the surface of said counter-bearing. Preferably, the branch also has an opening that communicates with the recess of the counter-bearing. In this way, gaseous of liquid fluids can escape unimpaired from the recess when the counter-bearing is compressed. A hardening of the counter-bearing due to fluids enclosed in the recess or even due to the coagulation of such fluids is prevented. Alternatively, the recesses may also be arranged so as to completely or partially extend through the cross-section of the counter-bearing.

Considering an alternative embodiment, it is possible to configure the branches with a closing element, e.g., a lid, relative to the recesses of the counter-bearing. In this case, the above-described fluids can either continue to exit from the recess of the counter-bearing or the closure element is designed in such a manner that they can continue to drain from the recesses of the counter-bearing.

The large-area open recess can allow the entering and then the re-exiting of fluids. The size of the opening prevents that, during operation in fluid (for example, blood), the compression and decompression of the counter-bearing causes a pumping action of the fluid. Even if, due to the thermal energy released on the instrument, fluid, for example blood, will coagulate and form clumps, the openings remain unobstructed toward the outside so that the continued inward and outward springiness is not impaired.

The surface of the counter-bearing that is located opposite the cutting element and that applies a force against the cutting element—optionally with the tissue in between—is referred to as the tissue support surface. The recess may be formed by a groove facing away from the tissue support surface or also by a row of short grooves separated from each other by transverse walls. Such a groove is laterally delimited by groove walls that bear the upper closed part of the counter-bearing that defines the tissue support surface. When the branches are being closed, the cutting electrode compresses the counter-bearing, as a result of which the recess located under the tissue support surface collapses at least in part.

Alternatively or additionally, one or more recesses may be provided, these extending through the tissue support surface and thus being open toward the branch that bears the cutting electrode. Such recesses may communicate with one or more recesses or hollow chambers of the counter-bearing on the rear side, i.e., facing away from the tissue support surface. The recesses or hollow chambers facing away from the tissue support surface are defined by walls diverging away from the tissue support surface. With this configuration, it is possible to achieve the desired characteristic line progression in a particularly easy and reliable manner. In doing so, the walls of the counter-bearing can (as also in other embodiments) display a constant wall thickness in the direction away from the tissue support surface.

The open recess formed on the counter-bearing and facing away from the tissue support surface may have one or more transverse walls. Such transverse walls may have a uniform wall thickness or also comprise a weakening region. The weakening region may also be omitted and represent a cutout. In doing so, the transverse wall no longer takes up the entire cross-section of the groove. When the counter-bearing is being compressed, a partial collapse of the recess may occur. With the use of the transverse walls a reduction of the force applied to the counter-bearing may be prevented due to the partial collapse of the recess. The transverse walls reinforce not only the total spring force of the counter-bearing but also generate the necessary force component so that the counter-bearing may also reset again in transverse direction when pressure is removed. The providing of the weakening region or a cutout in the transverse walls prevents a force increase that can result during the maximum compression against the stop and the resultant compression. Furthermore, the transverse walls also facilitate handling and the use of the counter-bearing that—in practical applications—is highly delicate because said transverse walls impart said counter-bearing with a basic stability and prevent a collapse of the entire structure in disassembled state.

In assembled state, the counter-bearing is held in place in the branch. To accomplish this, the counter-bearing may have lateral projections in the form of feet that are associated with complementary recesses in the branch. The laterally extending projections engage in the recesses of the branch and hold the counter-bearing. In addition, a holding element for fixation of the counter-bearing may be provided. This holding element displaces the walls of the counter-bearing having the feet away from each other in outward direction and ensures the firm seat of the feet in the recesses.

The material for the counter-bearing is preferably a biocompatible silicone having a hardness of 50 Shore, with which the desired spring force and above-describe plateau-like force progression of the force/path characteristic can be achieved. If recesses extending through the tissue support surface are provided, these are preferably arranged on both sides of a strip-shaped cutting electrode impact region of the tissue support surface. Preferably, a symmetrical form of the cross-section of the counter-bearing is achieved. This applies, in particular, when the cutting electrode impacts the counter-bearing in the center. Along the cutting electrode impact region of the tissue support surface it is possible to arrange strips on both sides, said strips preferably being flush with the cutting electrode impact region at the top. The strips may also be in contact with the inner flank of the branch and effect a centering of the counter-bearing—in inoperative state, as well as in spring-deflected state, i.e., completely or partially compressed state. The strips may be arranged at the same or changing distances and be arranged in pairs or not in pairs on both sides. It is also possible that the surface of the strips be configured in the form of a trough or wedge in order to enhance the centering function of the cutting element. It is also possible that the tissue support surface of the cutting electrode impact region be partially curved, trough-shaped or wedge-shaped in order to aid this centering function.

Due to the preferably planar joining of the strips to the cutting electrode impact region, it is furthermore prevented that the cutting element slides laterally off the cutting electrode impact region, as could happen in the event of an asymmetrical deformation of the counter-bearing. Such an asymmetrical deformation would also result in a lateral displacement of the cutting electrode. The supporting strips thus also stabilize the potentially laterally resilient cutting electrode and prevent it from tilting off. Consequently, they also ensure a symmetrical formation of the tissue accommodation spaces directly next to the cutting electrode, i.e., between the cutting electrode and the sealing electrodes.

Due to the desired behavior of the counter-bearing, namely the buckling of the lateral walls and, as it were, a snapping-over of the same, a symmetrical load on the counter-bearing must be ensured. An asymmetrical load could otherwise lead to an asymmetrical deformation of the counter-bearing. Here, the supporting strips fulfill an important function in that they minimize a lateral tilting-off, i.e., an oblique spring deflection of the cutting electrode impact region in the event of an asymmetrical load and thus an asymmetrical deformation. In doing so, the cutting electrode is prevented from sliding off to one side of the counter-bearing. Furthermore, the instrument becomes insensitive to forces that can occur during practical use when, for example, the grasped tissue is subjected to a lateral pull.

The branch bearing the cutting electrode has a tissue stop on the proximal end. This tissue stop may be integrated in the cutting element bearing the cutting electrode and prevent that—during the cutting of the tissue—parts of said tissue slide in the direction toward the hinge connecting the branches behind the cutting electrode of the cutting element. In doing so, a punched hole effect in the tissue is prevented and the entire, grasped tissue is also cut. To accomplish this, the counter-bearing may have a sliding region on its proximal end for this tissue stop that, preferably, has the form of a segment of a circle that is concentric to the hinge axis. Alternatively, the tissue stop may also be a part of the counter-bearing and slide along the cutting element. At any rate, the proximal side of the counter-bearing is formed in such a manner that it—irrespective of the position of the branches relative to each other—is always flush with the tissue stop.

With the inventive instrument, it is possible to adjust a cutting force of approximately 2 N to 4 N between the counter-bearing and the cutting electrode, said force acting on the tissue to be dissected when the branches are closed. As a result of this, the force acting on the cutting electrode can be minimized. In addition, it is ensured that the tissue is completely dissected. A film-like tissue part between the dissected tissue parts, as can occur in the prior-art application, is avoided due to ensuring a precise adjustment of the cutting force. Thus, the by far greatest part of the closing force of the branches that may be approximately 22 N in the center of the branch can be utilized for the sealing process. Consequently, the cutting force is only as great as necessary (approximately 2 N to 4 N), whereas the force existing on the sealing electrodes is as great as possible. Due to its resilience and thus spring-back potential, the counter-bearing applies only slightly more cutting force to the tissue between counter-bearing and cutting electrode than is necessary for cutting. The remaining closing force then is applied to the sealing electrodes. The above-described closing process of the instrument is applicable essentially independently of whether tissue is grasped or not grasped between the branches.

With the use of the said measure, favorable current density conditions on the cutting electrode are created. By correctly pressing the tissue against the cutting electrode a high current density on the cutting electrode is achieved, without mechanically dissecting the tissue. The resilience of the counter-bearing thus ensures that, when the tissue is being grasped and manipulated with the branch pair, the tissue—despite the narrow, angular cutting element—will be traumatized or mechanically damaged as little as possible. Furthermore, the counter-bearing acts as a tolerance compensation that always ensures that the large part of the closing force acts on the sealing electrodes and only a smaller part acts on the cutting electrode and the cutting element, respectively.

Due to the specific configuration of the counter-bearing there is also a certain mobility given in branch longitudinal direction that is within the range of the movements caused by the elastic deformation of the branches and the cutting element. This can be inferred from the brief description of the closing of the instrument hereinafter, where the closing force increases without tissue between the branches:

Initially, the cutting element contacts the tissue support surface of the counter-bearing directly on the proximal end. If force is continued to be applied, the counter-bearing collapses under the cutting element, in which case the cutting element and the branches may also deform slightly in an elastic manner. By closing, the counter-bearing is also slightly displaced in preferably distal branch longitudinal direction.

Ideally, the cutting element immerses in vertical direction and centered into the counter-bearing. The tissue support surface of the counter-bearing bulges inward—a recess is being formed. The oblique walls of the counter-bearing bulge outward in the direction toward the sealing electrodes. The upper sides of the supporting strips of the counter-bearing abut against the lateral surfaces of the cutting element, thus centering it in the center in the instrument. In doing so, the thickness and distances of the supporting strips are selected in such a manner that the recesses existing in between can act as tissue-accommodating spaces. The branches are completely closed when the sealing electrodes of the two branches are situated on top of each other, and the corresponding closing force of, for example, 22 N, is active in the branch center. In order to compensate for the elastic deformations of the branches, these are formed in such a manner that the sealing electrodes therefor first come into contact with each other on the distal end before the existing triangular gap is gradually closed by the increasing closing force and the resultant elastic deformation of the branches. The sealing electrodes of the branches may be configured relative to each other so as to define a parallel gap at a distance of 0.1 mm, for example. Inasmuch as no stops or spacers preventing further closing are provided, the gap becomes zero on the distal end during further closing. With increasing closing force, the branches then deform in an increasingly elastic manner, and the gap will, at some distance from the distal end, also become close to zero.

BRIEF DESCRIPTION OF THE DRAWINGS

The drawings show a few exemplary embodiments of the invention. They show in

FIG. 5 a perspective view, looking at the tissue support surface of the counter-bearing;

FIG. 6 the counter-bearing as in FIG. 5, looking at its underside recess;

FIG. 7 a schematic sketch illustrating the electric power supply of the instrument;

FIG. 8 the force/path characteristic (elasticity characteristic curve) of an infinitesimally small segment of the counter-bearing of the tool as in FIGS. 2 to 4;

FIGS. 9A-9C a cross-section of the tool in various positions when it is being closed.

DETAILED DESCRIPTION

Figure 1:
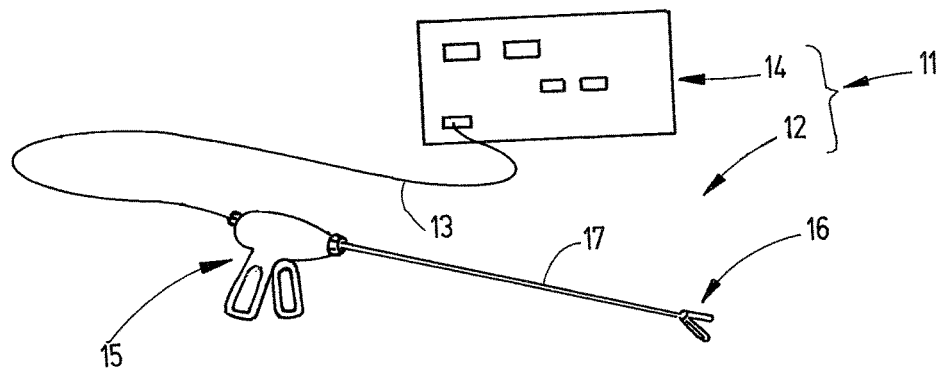
FIG. 1 a schematic illustration of an instrument for grasping, coagulating and dissecting biological tissue, said instrument being connected to a supply device.
Figure 2:
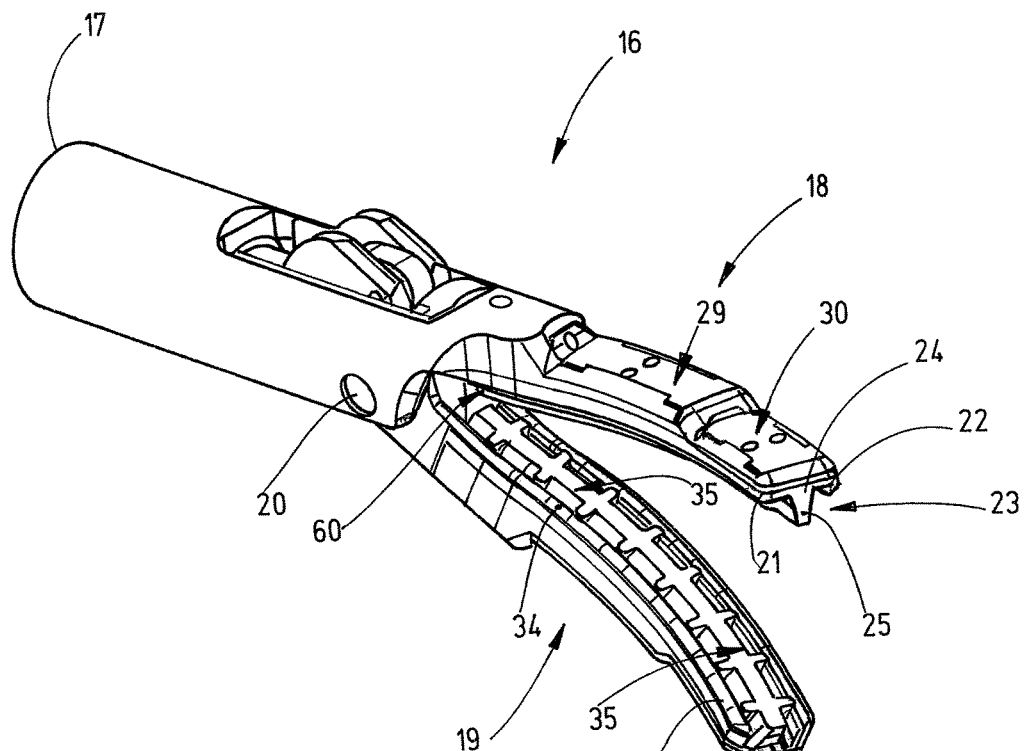
FIG. 2 an enlarged perspective illustration of the tool of the instrument, as in FIG. 1.

FIG. 1 shows an arrangement 11 that comprises an instrument 12 for grasping, coagulating and dissecting biological tissue, said instrument being connected to a supply device 14 via a cable 13. As shown, the instrument 12 may be configured so as to be an instrument for laparoscopic surgery or it may be otherwise configured. For example, it may be configured as a scissor-like instrument intended for open surgical procedures, as well as an instrument for endoscopic procedures. Furthermore, it may have a handle 15 for manual guidance or also a connection for machine guidance (not illustrated). Therefore, the instrument 12 can be guided directly by a user or by a robot. Independently thereof, it comprises a tool 16 that is arranged in the exemplary embodiment as in FIG. 1 on the distal end of an elongated shaft 17 of the instrument 12. The setup of the tool 16 will be explained hereinafter:

The tool 16 that is separately shown in FIG. 2 comprises—in FIG. 2—a first upper branch 18 and a second—in FIG. 2—lower branch 19 that are connected to each other at a hinge 20, so that at least one of the branches 18, 19 can be pivoted against the other one. Referring to the exemplary embodiment as in FIG. 2, the lower branch is movable.

Alternatively, both branches 18, 19 or also only the upper branch 19 may be configured so as to be movable. Inasmuch as the spatial orientation of the branches 18, 19 is a function of the position of the instrument 15, the upper branch 18 is referred to as the first branch and the lower branch 19 is referred to as the second branch hereinafter.

The first branch 18 preferably consists of an electrically conductive material, in particular metal, and has a U-shaped cross-section. Accordingly, a groove-like intermediate space is formed between two limbs 21, 22 that extend at a distance from each other, in which a cutting element 23 is arranged. Said cutting element consists of an electrically insulating material, for example a plastic material or ceramic. In its basic form, it has an approximately T-shaped cross-section. A middle wall section 25 having, on its narrow side facing the other branch 19, a cutting electrode, said middle wall section extending from a lower plateau-like foot section 24. This cutting electrode may be made of a metal plate that is inserted in the wall section 25 and held there. The cutting electrode 26 is exposed only on the side facing the other branch 19 of its cutting surface and does not, or only by a few tenths of a millimeter, extend beyond the narrow face side of the wall section 25.

Figure 3:
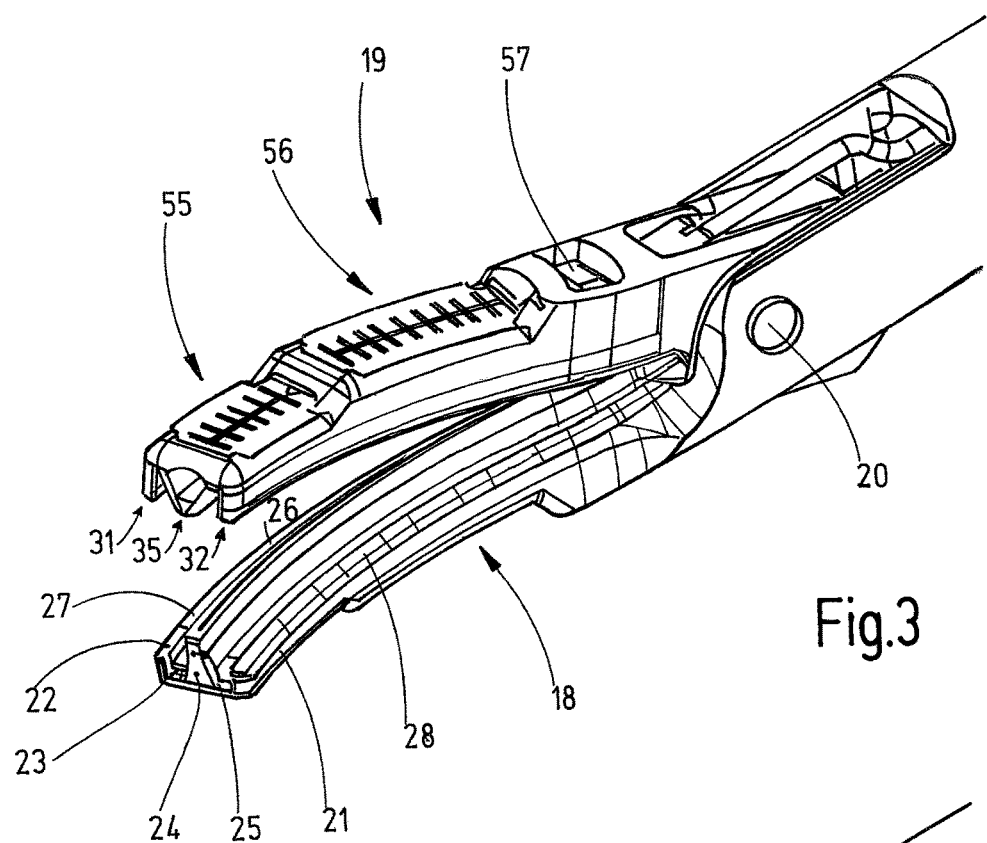
FIG. 3 a perspective illustration before fixation of the counter-bearing, in flipped position of the tool as in FIG. 2.
Figure 4:
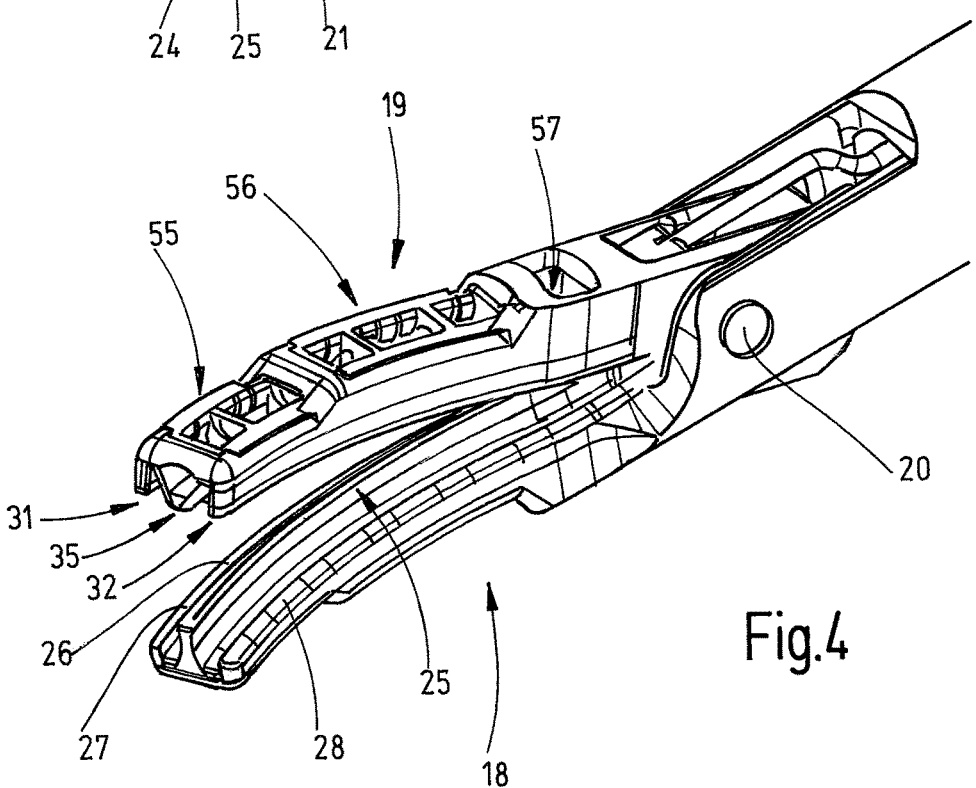
FIG. 4 the tool as in FIG. 3, with fixated counter-bearing.

The two limbs 21, 22 of the branch 19 are respectively formed by two lateral surfaces, one narrow side and an end surface arranged transversely with respect to this narrow side. Each limb 21, 22 comprises a first inner lateral surface and a second outer lateral surface. The two first inner lateral surfaces of the limbs 21, 22—together with a bottom surface—create the inner form of the U-shaped transverse section of the branch, namely the branch outside. The two long outer lateral surfaces—together with a back surface—create the outer form of the U-shaped cross-section of the branch. A plane that is supported on the two narrow sides of the limbs 21, 22 is arranged essentially parallel to the cutting surface of the cutting electrode 26. The sealing electrodes 27, 28 of the branch 19 are essentially located on the narrow side at an angle—preferably an acute angle—with respect to the first lateral surface of a limb 21, 22. The transition of a sealing electrode 27, 28 into the first and into the second lateral surface of the limbs 21, 22 is arcuate. In doing so, the radii of the two transitions may be different from each other. Preferably, the radius of the transition of a sealing electrode 27, 28 into the first inner lateral surface is smaller—in particular preferably 4× smaller—than the radius of the transition of a sealing electrode to the second lateral surface of the limb 21, 22. The sealing electrodes 27, 28 that are arranged on the narrow side of the limb extend over the previously described radii out into the first and the second lateral surfaces of the limbs 21, 22. The tool 16 comprises at least one sealing electrode 27, preferably however two such first sealing electrodes, between which the cutting element 23 with the cutting electrode 26 is arranged. In order to make this better understandable, the cutting element 23 with the cutting electrode 26 and the sealing electrodes 27, 28 are shown in FIGS. 3 and 4. As is shown by FIG. 2, the cutting element 23 may be anchored in a positive-locking manner in the branch 18 and, be secured, for example, by appropriate metal retaining plates 29, 30 against moving out on the rear side of the branch. In this case, the cutting element 23 is rigidly supported by the first branch 18, i.e., immovably supported. However, a movable bearing, is possible as a modification of each embodiment. Also, the cutting element 23 may itself allow a movement or be configured so as to be resilient or elastic.

The second branch 19—similar to the first branch as can be inferred from FIG. 2—has a U-shaped cross-section with limbs 31, 32, in which case the second sealing electrodes 33, 34 are arranged on the narrow sides of the two limbs 31, 32 of the U-cross-section. The sealing electrodes 33, 34 of the second branch 19—in closed condition of the instrument—are complementary to the sealing electrodes 27, 28 of the first branch, thus causing the formation of the acute angle between the sealing electrodes 33, 34 and the second lateral surface. Other than that, the description of the sealing electrodes 27, 28 is also applicable accordingly to the sealing electrodes 33, 34. The sealing electrodes 33, 34—like the first sealing electrodes 27, 28—can each be provided with a row of insulating fields, wherein the insulating fields of the first sealing electrodes 27, 28 are offset relative to the insulating fields of the second sealing electrodes 33, 34 in longitudinal direction of the electrodes so that an electrical short circuit is precluded in case the branches 18, 19 are touched.

Between the two limbs 31, 32 of the second branch 19, there is formed a groove-like free space in which is arranged a counter-bearing 35 that, preferably, is manufactured as a separate element. The counter-bearing 35 is shown separately and enlarged in FIGS. 5 and 6. Preferably, it is made of an elastic material such as, for example, an elastomer, silicone, silicone rubber, rubber or the like. On its side facing the cutting electrode 26, the counter-bearing 35 has a plane or slightly curved tissue support surface 36. When the counter-bearing is not compressed, the tissue support surface 36 is arranged so as to be essentially parallel to a plane located on the narrow sides of the limbs 31, 32. The tissue support surface 36 has a central strip-shaped cutting electrode impact region 54 that is directly opposite the cutting electrode 26 and is contacted by the cutting electrode 26 during the hinged closing of the tool 16.

The counter-bearing 35 is preferably made in one piece, for example, as an injection-molded, transfer-molded, pressed or sintered part, i.e., it consists seamlessly of a uniform material. Preferably, it has on its side facing away from the tissue support surface 36 a recess 37 (FIG. 6) that extends through a base surface 38 of the counter-bearing 35 and thus is open toward the outside. As can be inferred from FIG. 6, the recess 37 may be an elongated groove or the like that is divided into chambers by transverse walls 39, 40, 41, 42, 43. The transverse walls 39, 40, 41, 42, 43 may be arranged at equal or different distances relative to each other. They may be arranged at a right angle relative to the main base surface 38 or even be inclined with respect thereto.

The transverse walls 39, 40, 41, 42, 43 may have a section that is weakened, i.e., exhibiting a smaller wall thickness. It is also possible, as illustrated, to provide the transverse walls 39 to 43 on the bottom side with respectively one preferably arcuate, mouth-like recess 39a, 40a, 41a, 42a, 43a. By means of the size and the shape of the recess 39a, 40a, 41a, 42a, 43a it is possible to specifically define the transverse walls 39 to 43 and thus affect the resilience of the counter-bearing 35 overall. It is also possible to arrange the transverse walls 39 to 43 at a right angle with respect to the base surface 38 or also inclined with respect thereto. With this and with the size and shape of the recesses 39a, 40a, 41a, 42a, 43a, it is possible to control not only the resilience overall but also the form of the attainable elasticity characteristic curve and the deformation.

The recess 37 is laterally delimited in longitudinal direction by walls 44, 45 that, together with a roof section 46 bearing the tissue support surface 36, define a trapezoidal section of the groove or cutout 37. At the same time, the roof section 46 forms the bottom of the groove-like recess 37. The parts of the lateral walls 44, 45 delimiting the trapezoidal part of the recess 37 are inclined, preferably toward each other, and have a straight cross-section, as shown in FIG. 7. Referring to the exemplary embodiment according to FIG. 7, the lateral walls have a constant cross-section. The cross-sectional form affects the elasticity characteristic curve of the counter-bearing 35 and is able to take other forms to meet specific requirements Furthermore, the lateral walls 44, 45 may have sections extending parallel to each other, said sections having feet 47, 48 for fastening the counter-bearing 35 in the branch 19. Complementary recesses are provided in the branch 19 for the feet 47, 48, said recesses accommodating the feet 47, 48 in order to be secured therein.

Alternatively, the counter-bearing 35 may also be made of a silicone/metal composite component. In doing so, other fastening means than the above-described feet 47, 48 may be provided. These fastening means may be made of a material that is different from the elastic material that defines the elasticity characteristic curve of the counter-bearing. Nevertheless, the counter-bearing may be regarded as a one-piece component. If the counter-bearing 35 comprises fastening means of another type, the above-described recesses in the branch 19 may have a different configuration or be completely absent.

In addition to the recess 37, the counter-bearing 35 may have additional recesses. For example, such recesses 49, 50, 51, etc., may be formed on the on the side of the counter-bearing 35 facing away from the base surface 38. Such recesses 49 to 51 may be configured so as to extend through the tissue support surface 36 and be arranged so as to extend as a row on both sides of the counter-bearing 35 along its entire length. Between two neighboring recesses 49, 51 and 50, 52, respectively, centering strips 52, 53 may be formed, said strips being preferably dimensioned in such a manner that they—in starting state in the not deformed condition—abut against the inside flank of the respective limbs 31, 32 of the branch 19. On the upper side, the centering strips 52, 53, as well as the centering strips provided between the additional recesses, are flush with the tissue support surface 36. The centering strips 52, 53 have a double centering function: in not loaded state, they center the counter-bearing 35 between the sealing electrodes 33, 34 (FIGS. 7 and 9A) and, in closed state of the tool 16, they center the counter-bearing 35 relative to the cutting element 23 (FIG. 9C). It is also possible that the centering strips 52, 53 be rounded or oblique in the direction of the limbs 31, 32 in order to thus form more space for the accommodation of tissue within the closed branches 18, 19, without significantly changing the above-described centering functions.

Consequently, the tissue support surface 36 consists of the narrow, strip-shaped cutting electrode impact region 54 that extends along the length of the counter-bearing 35 and of the upper sides of the centering strips 52, 53 located on both sides. Between the centering strips 52, 53, among other things, there are respectively arranged pairs of recesses that correspond to the recesses 49 to 51 and may have a triangular cross-section.

The counter-bearing 35 that has been described so far is seated in a positive-locking manner in the branch 19 as can be inferred from FIG. 7. For fastening therein, the holding elements 55, 56, 57 shown in FIGS. 3 and 4 may be used, said holding elements abutting against the rear side of the branch 19 and extending by means of appropriate tabs 58, 59 through recesses provided in the branch 19 in order to fixate the counter-bearing 35. FIG. 3 illustrates the holding elements 55, 56, 57 before fixation, and FIGS. 4 and 7 after fixation. FIG. 7 shows two tabs 58, 59 of the holding element 57 as an example of the fixated state.

In accordance with the illustration of FIG. 2, the counter-bearing 35 and the cutting element 23 also form a tissue stop. For this, the cutting element 23 preferably has a tissue stop projection with a tissue support surface 60 that, preferably, follows an arc of a circle that is concentric to the hinge axis. The corresponding surface of the counter-bearing 35 on the proximal end has a complementarily matching counter-surface that, preferably, abuts without gap against the tissue stop surface 60.

The electrical wiring of the tool 16 is shown by FIG. 7. A suitable electric power source, for example in the form of an HF generator 61, provides electrical power, for example in the form of AC voltage of several hundred kHz. This voltage may be applied directly to the branches 18, 19, for example, and thus become active between the first sealing electrodes 27, 28 and the second sealing electrodes 33, 34. A transformer 62 supplied by the HF generator 61 can be used to transform the HF voltage up and supply the cutting electrode 26.

The instrument 12 and, in particular, the tool 16, operate as follows:

Hereinafter, an exemplary cross-section of the mouth part that closes like a hinge will be looked at. In open state or in the state closed without force of the viewed cross-section, the tool 16 is in the state as in FIGS. 7 and 9A. The cutting electrode 26 is in contact with the tissue support surface 36 without force and maintains the distance from said surface. Tissue grasped between the branches 18, 19 would be minimally or not deformed in this cross-section.

If, in the viewed cross-section, the branches 18, 19 are now moved further toward each other—as is shown without tissue grasped in the FIG. 9B—the first sealing electrodes 27, 28 approach the second sealing electrodes 33, 34. Tissue grasped between them is pinched together and deformed. Furthermore, current is applied to the tissue and it is thus cut and coagulated. In doing so, the counter-bearing 35 ensures due to its elasticity that, despite tissue shrinkage, there is always tissue in contact with the cutting electrode until said tissue is cut completely.

If there is no tissue between the branches, the cutting electrode 26 presses against the tissue support surface 36 and deforms the counter-bearing 35. While this takes place, the force directed by the counter-bearing 35 against the cutting electrode 26 increases gradually, as is illustrated in FIG. 8, in a first section I of the depicted curve in order to then reach a plateau in section II. This illustration of the diagram according to FIG. 8 relates to an infinitesimally small cross-sectional segment of the branches of the instrument. The forces indicated in the diagram relate to the entire length of the counter-bearing element, over the extrapolated (e.g., added up) values over all the infinitesimal elements. Alternatively, this characteristic can also be determined in that the first branch and the second branch are moved toward each other (closed) in a parallel direction.

When the branches 18, 19 are continued to be brought together in the viewed cross-section, the counter-bearing 35 deforms as shown in FIG. 9C. The strips 52, 53 are lifted off the insides of the limbs 31, 32 and come into contact with the lateral surfaces of the wall section 25. In doing so, the lateral walls 44, 45 buckle increasingly as is shown by a comparison of FIGS. 9A to 9C, and the transverse wall 39 is correspondingly displaced downward. Finally, the branches move onto each other, or the sealing electrodes 27, 28 and 33, 34 and the mouth part are closed. Starting at this point, no further compression of the counter-bearing occurs, unless there is still tissue in the mouth part. In this case, a part of the counter-bearing 35, e.g., the transverse wall 39, can come into contact with at least one of the metal retaining plates 55 to 57. As a result, a force increase III can be observed after passing through the plateau II in FIG. 8.

While the tissue is being cut or when the closed mouth part is reopened, the deformed counter-bearing 35 will rise again. The resetting force of the counter-bearing 35 in the viewed cross-section decreases again; see curve IV. As soon as all parts of the counter-bearing 35 that are supported by the metal retaining plates 55 to 57 are lifted again, a deformation with relatively constant force occurs, thus corresponding to the curve progression V. The force applied by the counter-bearing 35 against the cutting electrode 26 in this resetting plateau region V would be—when viewing an idealized parallel closure—in the range of 2 N to 4 N in the branch center. A hysteresis may occur due to the energy loss in the elastic material in the force/path progression.

If, while the mouth parts are being closed, there still is tissue to be cut present between the cutting electrode 26 and the tissue support surface 36, the counter-bearing 35 will deform already before the cutting electrode 26 comes into contact with the tissue support surface 36. If activation is started, the cutting and sealing processes occur at the same time. During the cutting and sealing processes different tissue movements occur at different points. If the tissue to be cut gradually yields due to the cutting operation, the tissue support surface 36 approaches the cutting electrode 26 more and more. At this point the resetting force of the counter-bearing 35 specifies the cutting force and essentially ensures the cutting movement. With the branches 18, 19 closed—with or without tissue—the counter-bearing 35 is completely inside the outside mold of the mouth part that is being formed by the branches 18, 19. With the mouth part closed, the counter-bearing does not extend beyond the branch outsides at any point. With the branches 18, 19 closed, the counter-bearing extends—neither in relaxed nor in compressed state—beyond the rear surface of the branch 19 in which said counter-bearing is held.

In contrast, the total closing force applied to the branches 18, 19 is considerably greater than the force between the counter-bearing 35 and the cutting electrode 26 and may be, for example, 10 N to 30 N, for example 22 N, in the center of the branch. Independently thereof, the counter-bearing 35 sets a force of 2 N to 8 N on the cutting electrode 26, so that the residual force between the sealing electrodes 27, 33 and 28, 34, respectively, becomes effective. In this manner it is possible to accomplish two things: a secure seal and coagulation due to higher forces and a clean cut performed essentially purely electrically. The aforementioned values of the closing force are a function of the design, in particular the size of the branches of the surgical instrument. Changed geometric conditions, for example for open surgical or machine-controlled applications may result in different closing force values.

Figure 10:
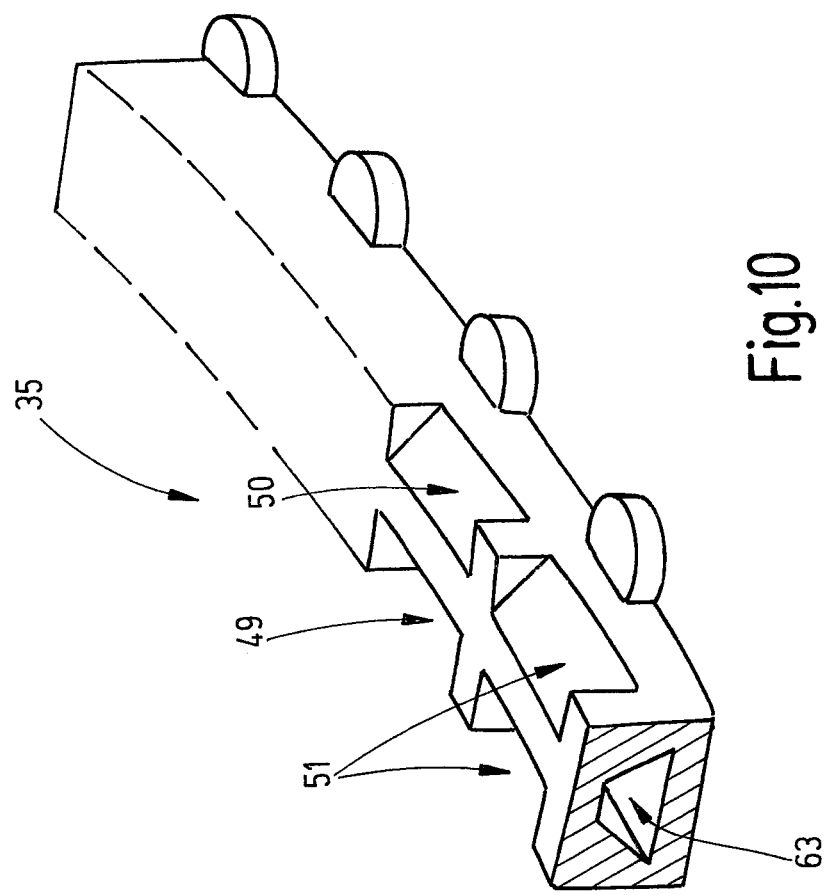
FIG. 10 a schematized perspective illustration of a modified embodiment of the counter-bearing.

Instead of the open recess 37, the counter-bearing 35 may also have a hollow chamber 63, as shown in FIG. 10. In addition, recesses 49 to 51 may be provided. However, such recesses may be omitted. The hollow chamber 63 may be round, trapezoidal, rectangular, star-shaped or be configured in similar forms.

Instead of a single large chamber, it is also possible to provide a plurality of small chambers, for example in that the body of the counter-bearing 35 is generally, or in zones, configured as an open-cell or closed-cell foam.

In an inventive tool 16 for the coagulation and dissection of biological tissue there is provided a counter-bearing 35 that has at least one recess 37 open toward the outside and/or one or more hollow chambers 63. The recess 37 or the hollow chamber 63 is configured in such a manner that the counter-bearing 35—when viewing an infinitesimally small cross-sectional segment—generates a force/path elasticity characteristic curve with a plateau-like region II, V, during compression and reexpansion. On this plateau II, V, the counter-bearing 35—when viewing an idealized parallel contact of the counter-bearing and the cutting electrode—preferably provides a force between 2 N and 4 N. The path section x in which the elasticity characteristic curve indicates the plateau II, IV preferably is as long as the tissue to be dissected is thick, and is, for example, in the range of 0.2 to 1.5 mm; preferably, the thickness is 1 mm, particularly preferably 0.5 mm. As a result of this, it is achieved that the force exerted on the tissue during the cutting operation remains substantially constant in the effective work region.

LIST OF REFERENCE SIGNS

| | |
|---|---|
| 11 | Arrangement |
| 12 | Instrument |
| 13 | Cable |
| 14 | Device for supplying the instrument |
| 15 | Handle |
| 16 | Tool |
| 17 | Shaft |
| 18 | First (upper) branch |
| 19 | Second (lower) branch |
| 20 | Hinge |
| 21, 22 | Limb of the U-cross-section of the first branch 18 |
| 23 | Cutting element |
| 24 | Foot section |
| 25 | Wall section |
| 26 | Cutting electrode |
| 27, 28 | First coagulation, sealing electrode |
| 29, 30 | Metal retaining plate |
| 31, 32 | Limb of the U-cross-section of the second branch 19 |
| 33, 34 | Second coagulation, sealing electrode |
| 35 | Counter-bearing |
| 36 | Tissue support surface |
| 37 | Recess |
| 38 | Base area |
| 39-43 | Transverse walls |
| 39a-43a | Recesses of the transverse walls 39, 40, 41, 42, 43 |
| 44, 45 | Lateral walls/bottom of the recess 37 |
| 46 | Roof section, bottom |
| 47, 48 | Feet |
| 49-51 | Recesses |
| 52, 53 | Centering strips |
| 54 | Cutting electrode impact region |
| 55-57 | Holding element |
| 58, 59 | Tabs |
| 60 | Tissue support surface |
| 61 | HF generator |
| 62 | Transformer |
| 63 | Hollow chamber |

The invention claimed is:

1. An instrument (12) for grasping, coagulating and dissecting biological tissue, comprising a first branch (18) on which is provided at least one first sealing electrode (27, 28), a second branch (19) on which is provided at least one second sealing electrode (33, 34), wherein at least one of the first branch or the second branch is movably arranged in order to move the first and second branches (18, 19) toward each other and away from each other, and a cutting electrode (26) that is arranged on one of the first branch or the second branch, a counter-bearing (35) that is arranged on one of the first branch or the second branch not having the cutting electrode and is made of an elastic material and has a tissue support surface (36) facing the cutting electrode (26), wherein the tissue support surface (36) has at least a section extending broader than a wall section (25) supporting the cutting electrode (26), the tissue support surface (36) configured to have at least a portion thereof deform around and contact lateral surfaces of the wall section (25) when the branches (18, 19) are closed, wherein the counter-bearing (35) defines a surface (46) opposite of the tissue support surface (36) and groove walls facing each other and extending from the surface (46) opposite of the tissue support surface (36), the groove walls having at least a first portion extending from and tapering toward the surface (46) opposite of the tissue support surface (36), the surface (46) opposite of the tissue support surface (36) and the groove walls defining a first recess (37) facing away from the cutting electrode (26) or at least a portion of at least one hollow chamber (63) within the counter-bearing (35), wherein the counter-bearing (35) defines a plurality of outer recesses (49-51) that open toward an outside of the one of the first branch or the second branch on which the counter bearing (35) is arranged, wherein at least two of the plurality of outer recesses (49-51) of the counter-bearing (35) are arranged so as to extend through the tissue support surface (36) and further arranged outside a cutting electrode impact region (54) of the tissue support surface (36) on which the cutting electrode sits with the first and second branches (18, 19) closed, wherein the at least two of the plurality of outer recesses (49-51) are arranged along both sides of the cutting electrode impact region (54).

2. The instrument as in claim 1, wherein the surface (46) opposite of the tissue support surface (36) and the groove walls define a groove facing away from the tissue support surface (36) and laterally delimited by the groove walls that support the tissue support surface (36).

3. The instrument as in claim 1, wherein the first recess (37) is arranged so as to extend fully or partially through a cross-section of the counter-bearing.

4. The instrument as in claim 2, wherein at least one transverse wall (39-43) is arranged in the groove transverse to the groove walls.

5. The instrument as in claim 1, wherein the counter-bearing (35) has laterally projecting feet (47, 48) that are associated with complementary recesses in the one of the first branch or the second branch (18, 19) on which the counter-bearing (35) is arranged.

6. The instrument as in claim 1, wherein the one of the first branch or the second branch (18, 19) on which the counter-bearing (35) is arranged has a branch recess facing away from the counter-bearing (35), where at least one holding element (55-57) is arranged for retaining the counter-bearing (35).

7. The instrument as in claim 1, wherein the counter-bearing (35), in relaxed or compressed state with the first and second branches (18, 19) closed, does not reach beyond a branch recess of the one of the first branch or the second branch (18, 19) facing away from the counter-bearing (35).

8. The instrument as in claim 6, wherein the counter-bearing (35), in relaxed or compressed state with the first and second branches (18, 19) closed, does not reach beyond a branch recess of the one of the first branch or the second branch (18, 19) facing away from the counter-bearing (35) and the holding element (55-57) has tabs (58, 59) that are arranged so as to extend into the first recess (37) of the counter-bearing (35) to hold lateral feet (47, 48) in complementary recesses in the one of the first branch or the second branch (18, 19) on which the counter-bearing (35) is arranged.

9. The instrument as in claim 1, wherein the counter-bearing (35) comprises centering strips (52, 53) configured so as to abut against lateral surfaces of a groove formed in the branch (19).

10. The instrument as in claim 1, wherein the counter-bearing (35)—when viewing an infinitesimally small cross-sectional segment—has a non-linear elasticity characteristic curve with a plateau.

11. The instrument as in claim 1, wherein the elastic material is a material of the group comprising silicones.

12. The instrument as in claim 1, wherein the counter-bearing (35) comprises centering strips (52, 53) and the counter-bearing (35) is configured to deform during closing of the branches (18, 19) such that the centering strips (52, 53) move to center the cutting electrode (26).

13. The instrument as in claim 12, wherein the counter-bearing (35) is configured to deform such that the centering strips (52, 53) move toward both sides of the cutting electrode (26) to center the cutting electrode (26).

* * * * *